(12) United States Patent
Hu et al.

(10) Patent No.: US 12,268,711 B2
(45) Date of Patent: Apr. 8, 2025

(54) **METHODS FOR PREPARING PRODUCTS FOR TREATING SCALD INFECTION CAUSED BY *PSEUDOMONAS AERUGINOSA***

(71) Applicant: NINGBO EISEN LIFE TECHNOLOGY CO., LTD., Zhejiang (CN)

(72) Inventors: Liangbin Hu, Ningbo (CN); Haizhen Mo, Ningbo (CN); Xiaohui Zhou, Ningbo (CN); Hongbo Li, Ningbo (CN); Dan Xu, Ningbo (CN); Zhenbin Liu, Ningbo (CN); Zhen Wang, Ningbo (CN)

(73) Assignee: NINGBO EISEN LIFE TECHNOLOGY CO., LTD., Ningbo (CN)

( * ) Notice: Subject to any disclaimer, the term of this patent is extended or adjusted under 35 U.S.C. 154(b) by 0 days.

(21) Appl. No.: 18/777,570

(22) Filed: Jul. 19, 2024

(65) Prior Publication Data
US 2025/0049844 A1 Feb. 13, 2025

(30) Foreign Application Priority Data
Aug. 7, 2023 (CN) .......................... 202310986080.1

(51) Int. Cl.
| | | |
|---|---|---|
| *A61K 33/26* | (2006.01) | |
| *A61K 9/06* | (2006.01) | |
| *A61K 31/375* | (2006.01) | |
| *A61K 47/36* | (2006.01) | |
| *A61P 17/02* | (2006.01) | |

(52) U.S. Cl.
CPC ................ *A61K 33/26* (2013.01); *A61K 9/06* (2013.01); *A61K 31/375* (2013.01); *A61K 47/36* (2013.01); *A61P 17/02* (2018.01)

(58) Field of Classification Search
CPC ........ A61K 33/26; A61K 9/06; A61K 31/375; A61K 47/36; A61P 17/02
See application file for complete search history.

(56) References Cited

U.S. PATENT DOCUMENTS

2022/0000912 A1  1/2022  Morrison et al.

FOREIGN PATENT DOCUMENTS

| CN | 1207901 A | 2/1999 |
|---|---|---|
| CN | 102525888 A | * 7/2012 |
| CN | 105194364 A | 12/2015 |
| CN | 116421551 A | 7/2023 |

OTHER PUBLICATIONS

First Office Action in Chinese Application No. 202310986080.1 mailed on Dec. 22, 2023, 21 pages.
Notification to Grant Patent Right for Invention in Chinese Application No. 202310986080.1 mailed on Mar. 13, 2024, 5 pages.
Feng, Chengyuan et al., The Sterilization of Ferric Salts on Cronobacter Sakazakii, Journal of Henan University of Technology (Natural Science Edition), 43(4): 9-17, 2022.

* cited by examiner

*Primary Examiner* — Jessica Worsham
(74) *Attorney, Agent, or Firm* — PORUS IP LLC

(57) ABSTRACT

Disclosed is a method for preparing a product for treating scald infection caused by *Pseudomonas aeruginosa*. The product includes a ferrous sulfate hydrogel, the scald is a deep second-degree scald or a third-degree scald, and a preparation process of the ferrous sulfate hydrogel includes: S1, obtaining a mixed solution by dissolving ferrous sulfate and vitamin C at a concentration ratio of 1:1 in sterile ultrapure water, heating the mixed solution to 50° C., and a concentration of the ferrous sulfate in the mixed solution being 2 mM, and S2, under a condition of heating, continuing to add sodium alginate powder whose mass constitutes 3.5% of a total mass of the mixed solution, stirring until the sodium alginate powder is dissolved and forming a stable colloid, and obtaining 2 mM of the ferrous sulfate hydrogel.

3 Claims, 8 Drawing Sheets

| Group of a hydrogel | Group of a hydrogel containing VC and FeSO$_4$ | |
|---|---|---|
| | 1mM | 2mM |
|  |  |  |

METHODS FOR PREPARING PRODUCTS FOR TREATING SCALD INFECTION CAUSED BY *PSEUDOMONAS AERUGINOSA*

CROSS-REFERENCE TO RELATED APPLICATIONS

This application claims priority to Chinese patent application No. 202310986080.1, filed on Aug. 7, 2023, the entire contents of which are incorporated herein by reference.

TECHNICAL FIELD

The present disclosure relates to the field of biomedical technology, and in particular, to a method for preparing a product for treating scald infection caused by *Pseudomonas aeruginosa*.

BACKGROUND

Factors such as scald and surgical manipulation are the most common causes of wound infections in patients, and many wounds, if not properly prevented and controlled for infection, may further lead to adverse consequences such as difficulty in healing, deep tissue infections, and even systemic infection. In the case of scald wounds, the presence of large amounts of necrotic and degenerated tissue disrupts the natural barrier of skin against microbial invasion, making it susceptible to bacterial colonization. When the bacteria invade the exudate or necrotic tissues on the skin surface and reach a certain amount, systemic symptoms such as septic infections and sepsis tend to occur. For surgical operations, patients with traumatic injuries are susceptible to secondary infections after undergoing an open procedure due to lowered autoimmunity. These secondary infections have now become a key concern for postoperative health management in hospitals.

Common wound infection pathogens include *Pseudomonas aeruginosa* (PA), *Staphylococcus aureus*, *Acinetobacter baumannii*, and *Fusobacterium citriodora*, with *Pseudomonas aeruginosa* infection being the most common. Antibiotic therapy is still commonly used to treat *Pseudomonas aeruginosa* infections. Currently, the common treatments available for *Pseudomonas aeruginosa* scald infection are mainly medical antibiotic hydrogels and some essential topical steroidal ointments, such as ciprofloxacin hydrochloride hydrogel, gentamicin sulfate hydrogel, and silver sulfadiazine ointment. Although antibiotic therapy possesses high efficiency and low-dose bactericidal efficacy in eliminating pathogenic bacteria of infections, it still suffers from following problems: 1) it does not have a positive effect on the healing of skin wounds; 2) the high use of antibiotics exacerbates the risk of bacterial resistance, and drug dependence leads to an increase in the dosage of the drug, which creates a vicious circle. When the human body is repeatedly infected with bacteria, the resistance to that antibiotic ointment will make the antibiotic ineffective, i.e., unregulated use as well as misuse of antibiotics will enhance the human body's resistance to antibiotics, and 3) antibiotic treatment may not effectively prevent bacteria from migrating and colonizing in the body, which may easily cause lesions in other tissues and organs.

In recent years, there has been an increasing clinical interest in the study of colonization interventions for multidrug-resistant *Pseudomonas aeruginosa* (MRPA). Open wounds have a high rate of MRPA colonization and a long course of infection, which is relatively tricky to deal with and has a large physiological and psychological impact on patients. Therefore, there is an urgent need to find a new antimicrobial therapy to address this problem.

SUMMARY

One or more embodiments of the present disclosure may provide a method of preparing a product for treating scald infection caused by *Pseudomonas aeruginosa*. The product may include a ferrous sulfate hydrogel, the scald may be a deep second-degree scald or a third-degree scald, and a preparation process of the ferrous sulfate hydrogel may include S1, obtaining a mixed solution by dissolving ferrous sulfate and vitamin C ($V_C$) at a concentration ratio of 1:1 in sterile ultrapure water, and heating the mixed solution to 50° C., wherein a concentration of the ferrous sulfate in the mixed solution is 2 mM, and S2, under a condition of heating, continuing to add sodium alginate powder whose mass constitutes 3.5% of a total mass of the mixed solution, stirring until the sodium alginate powder is dissolved and forming a stable colloid, and obtaining 2 mM of the ferrous sulfate hydrogel.

In some embodiments, the product may be a therapeutic medication for the scald infection and/or a scald care product.

In some embodiments, the product may further include other medications for the treatment of the scald infection.

BRIEF DESCRIPTION OF THE DRAWINGS

The present disclosure is further illustrated in terms of exemplary embodiments, and these exemplary embodiments are described in detail with reference to the drawings. These embodiments are not restrictive, where.

DETAILED DESCRIPTION

Figure 1:
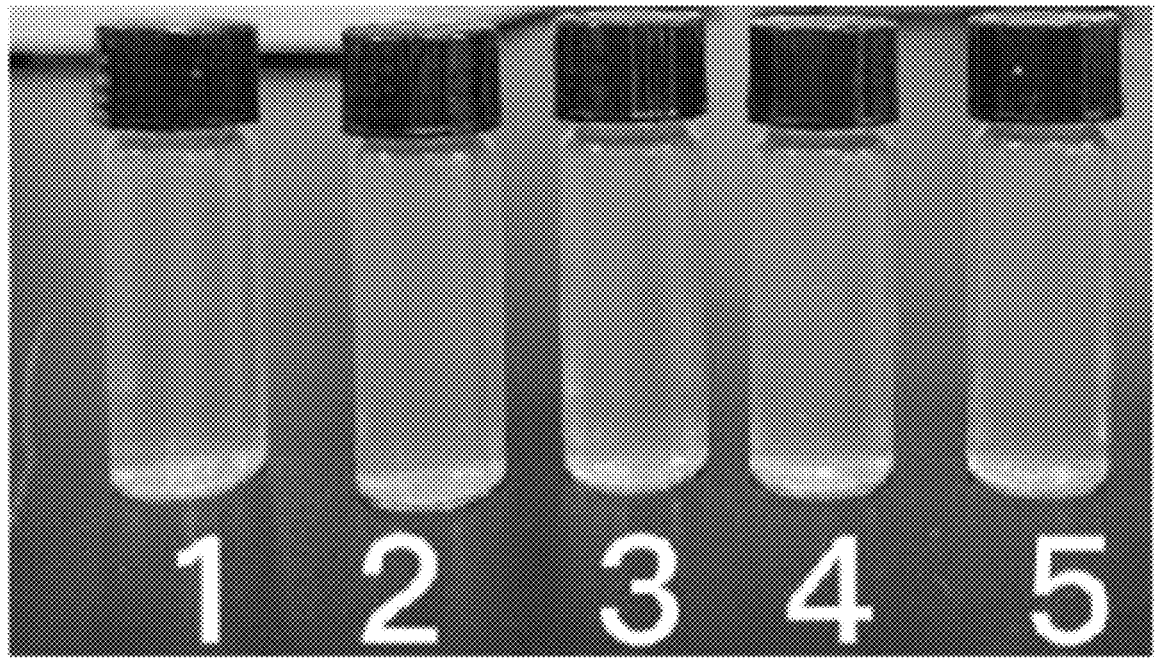
FIG. 1 is a diagram illustrating images of hydrogels of different treatment groups according to some embodiments of the present disclosure.

In order to illustrate the technical solutions related to the embodiments of the present disclosure, a brief introduction of the drawings referred to in the description of the embodiments is provided below. Obviously, drawings described below are only some examples or embodiments of the present disclosure. Those having ordinary skills in the art, without further creative efforts, may apply the present disclosure to other similar scenarios according to these drawings. Unless stated otherwise or obvious from the context, the same reference numeral in the drawings refers to the same structure and operation.

As shown in the present disclosure and claims, unless the context clearly indicates exceptions, the words "a," "an," "one," and/or "the" do not specifically refer to the singular, but may also include the plural. The terms "including" and "comprising" only suggest that the steps and elements that have been clearly identified are included, and these steps and elements do not constitute an exclusive list, and the method or device may also include other steps or elements.

One or more embodiments of the present disclosure provide a method of preparing a product for treating scald infection caused by *Pseudomonas aeruginosa* (PA). The product includes a ferrous sulfate hydrogel, and a preparation process of the ferrous sulfate hydrogel includes: S1, obtaining a mixed solution by dissolving ferrous sulfate and vitamin C at a concentration ratio of 1:1 in sterile ultrapure water, and heating the mixed solution to 50° C., and a concentration of the ferrous sulfate in the mixed solution being 2 mM, and S2, under a condition of heating, continuing to add sodium alginate powder whose mass constitutes 3.5% of a total mass of the mixed solution, stirring until the sodium alginate powder is dissolved and forming a stable colloid, and obtaining 2 mM of the ferrous sulfate hydrogel.

In some embodiments, the ferrous sulfate hydrogel may include ferrous sulfate, a protective agent, a solvent, or the like.

In some embodiments, an amount of the ferrous sulfate may be 1 mM-2 mM. In some embodiments, the amount of the ferrous sulfate may be 1 mM or 2 mM.

In some embodiments, the protective agent may be vitamin C, and an amount of the vitamin C may be 1 mM-2 mM. In some embodiments, the amount of the vitamin C may be 1 mM or 2 mM.

In some embodiments, the solvent may be at least one of carrageenan, xanthan gum, low acyl colloids, sodium alginate, hyaluronic acid, carbomer, or physiological saline.

In some embodiments, the solvent may be sodium alginate, and an amount of the sodium alginate may occupy 2%-3.5% of the ferrous sulfate hydrogel. In some embodiments, the amount of the sodium alginate may occupy 2% or 3.5% of the ferrous sulfate hydrogel.

In some embodiments, the scald infection may be a deep second-degree scald or a third-degree scald infection.

In some embodiments, the scald infection may be scald infection caused by *Pseudomonas aeruginosa* (PA).

In some embodiments, the scald infection may be scald infection caused by multidrug-resistant *Pseudomonas aeruginosa* (MRPA).

In some embodiments, the product may be a therapeutic medication for the scald infection and/or a scald care product.

In some embodiments, the product may further include other medications for the treatment of the scald infection.

Embodiments of the present disclosure have following beneficial effects:

(1) The embodiments of the present disclosure use a hydrogel as a carrier of ferrous ions and use a hydrogel containing ferrous ions in the treatment of scald. Through in vitro bacteriostatic activity experiments, it is found that a hydrogel containing 2 mM of ferrous ions has a bactericidal rate as high as 99.9% against *Pseudomonas aeruginosa*, and the bactericidal ability of the hydrogel containing ferrous ions is significantly higher than that of antibiotics; (2) Through animal experiments, it is found that compared with an infection group, an antibiotic group, and a scald ointment group, wounds of scalded rats are completely healed, accompanied by a large amount of hair growth and complete epidermal generation after 15 days of treatment with the hydrogel containing ferrous ions, which indicates that the hydrogel containing ferrous ions has an efficient bactericidal effect against *Pseudomonas aeruginosa*, and can effectively promote the healing of scald wounds and the generation of epidermis. (3) The hydrogel containing ferrous ions is cheaper than current antibiotic treatments and does not develop resistance, which can be used as a drug to combat the current antibiotic problem.

The experimental techniques in the following examples, unless otherwise specified, are conventional techniques. The test materials used in the following examples, unless otherwise specified, are obtained from standard biochemical reagent companies.

Quantitative assays in the following examples are performed with three replicate experiments, and the results are averaged. Embodiments of the present disclosure are further described below in connection with specific embodiments.

EXAMPLES

Example 1. In Vitro Bacteriostatic Activity of Ferrous Ions

Step 1, preparation of different groups of hydrogels
(1) Group of a Hydrogel (Blank Group)

Sterile ultrapure water was heated to 50° C. Subsequently, sodium alginate powder whose mass constitutes 2% of a total mass of the sterile ultrapure water was slowly added, stirring was performed until the sodium alginate powder dissolved and a stable colloid was formed, and a hydrogel was obtained.

(2) Group of a Hydrogel Containing Ferrous Sulfate

S1, ferrous sulfate ($FeSO_4$) at a concentration of 1 mM was dissolved in sterile ultrapure water to obtain a ferrous sulfate solution, and the ferrous sulfate solution was heated to 50° C. to obtain a mixed solution;

S2, under a condition of heating, sodium alginate powder whose mass constitutes 2% of a total mass of the mixed solution was added, stirring was performed until the sodium alginate powder was dissolved and a stable colloid was formed, and a ferrous sulfate hydrogel was obtained.

(3) Group of a Hydrogel Containing Antibiotics

S1, ciprofloxacin hydrochloride at a concentration of 1 mg/mL was dissolved in sterile ultrapure water to obtain a mixed solution, and the mixed solution was heated to 50° C.;

S2, under a condition of heating, sodium alginate powder whose mass constitutes 2% of a total mass of the mixed solution was added, stirring was performed until the sodium alginate powder was dissolved and a stable colloid was formed, and a hydrogel containing 1 mg/mL of the ciprofloxacin hydrochloride was obtained.

(4) Group of a Hydrogel Containing 1 mM of Vitamin C ($V_C$) and Ferrous Sulfate S1, ferrous sulfate ($FeSO_4$) and vitamin C at a concentration ratio of 1:1 were dissolved in sterile ultrapure water to obtain a mixed solution, and the mixed solution was heated to 50° C., and a concentration of the ferrous sulfate in the mixed solution was 1 mM;

S2, under a condition of heating, sodium alginate powder whose mass constitutes 2% of a total mass of the mixed solution was added, stirring was performed until the sodium alginate powder was dissolved and a stable colloid was formed, and a hydrogel containing 1 mM of vitamin C and ferrous sulfate was obtained.

(5) Group of a Hydrogel Containing 2 mM of Vitamin C and Ferrous Sulfate

S1, ferrous sulfate and vitamin C at a concentration ratio of 1:1 were dissolved in sterile ultrapure water to obtain a mixed solution, and the mixed solution was heated to 50° C., and a concentration of the ferrous sulfate in the mixed solution was 2 mM;

S2, under a condition of heating, sodium alginate powder whose mass constitutes 3.5% of the mass of the mixed solution was added, and stirring was performed until the sodium alginate powder was dissolved and a stable colloid was formed, and a hydrogel containing 2 mM of vitamin C and ferrous sulfate was obtained.

Step 2, the group of the hydrogel, the group of the hydrogel containing ferrous sulfate, the group of the hydrogel containing antibiotics, the group of the hydrogel containing 1 mM of vitamin C and ferrous sulfate, and the group of the hydrogel containing 2 mM of vitamin C and ferrous sulfate were poured into sterile disposable petri dishes, respectively, and set aside.

Prepared spare hydrogels are shown in FIG. 1, which illustrates images of hydrogels of different treatment groups. In FIG. 1, No. 1 represents the group of the hydrogel, No. 2 represents the group of the hydrogel containing ferrous sulfate, No. 3 represents the group of the hydrogel containing 1 mM of vitamin C and ferrous sulfate, No. 4 represents the group of the hydrogel containing 2 mM of vitamin C and ferrous sulfate, and No. 5 represents the group of the hydrogel containing 1 mg/mL of the ciprofloxacin hydrochloride. Due to the instability of ferrous sulfate, the hydrogel containing only ferrous sulfate (No. 2 in FIG. 1) is oxidized to trivalent iron as a result of heating, stirring and other factors in the process of preparation of active ingredient ferrous sulfate in the hydrogel, and the generation of the trivalent iron weakens a bactericidal activity of the hydrogel in the present disclosure. Therefore, vitamin C is selected as a protective agent for improvement, and the hydrogel containing vitamin C and ferrous sulfate (No. 3 and No. 4 in FIG. 1) is prepared, which can greatly slow down the oxidation of the ferrous sulfate and ensure a bactericidal activity of the ferrous sulfate.

Step 3, $10^8$ CFU/mL of PA was washed twice with physiological saline and collected into round sterile filter paper with a diameter of 1 cm, respectively; the round sterile filter paper with PA cells was placed face up in each petri dish in step 2, and each petri dish was sealed and incubated in a 37° C. incubator for 12 h. Then the filter papers were carefully taken out with sterile tweezers, and excessive hydrogels on backs of the filter papers were wiped off with a sterile cotton swab, and the filter papers were placed in sterile EP tubes, respectively. 1 mL of sterile saline was added to the sterile EP tubes, and ultrasonication was carried out for 30 s. Cells on the filter papers were collected, and finally a total number of bacterial colonies was determined by a drop plate manner.

In addition, in line with the above method, the bactericidal effect of each group of hydrogels against multidrug-resistant *Pseudomonas aeruginosa* (MRPA) was also tested.

Figure 2A:
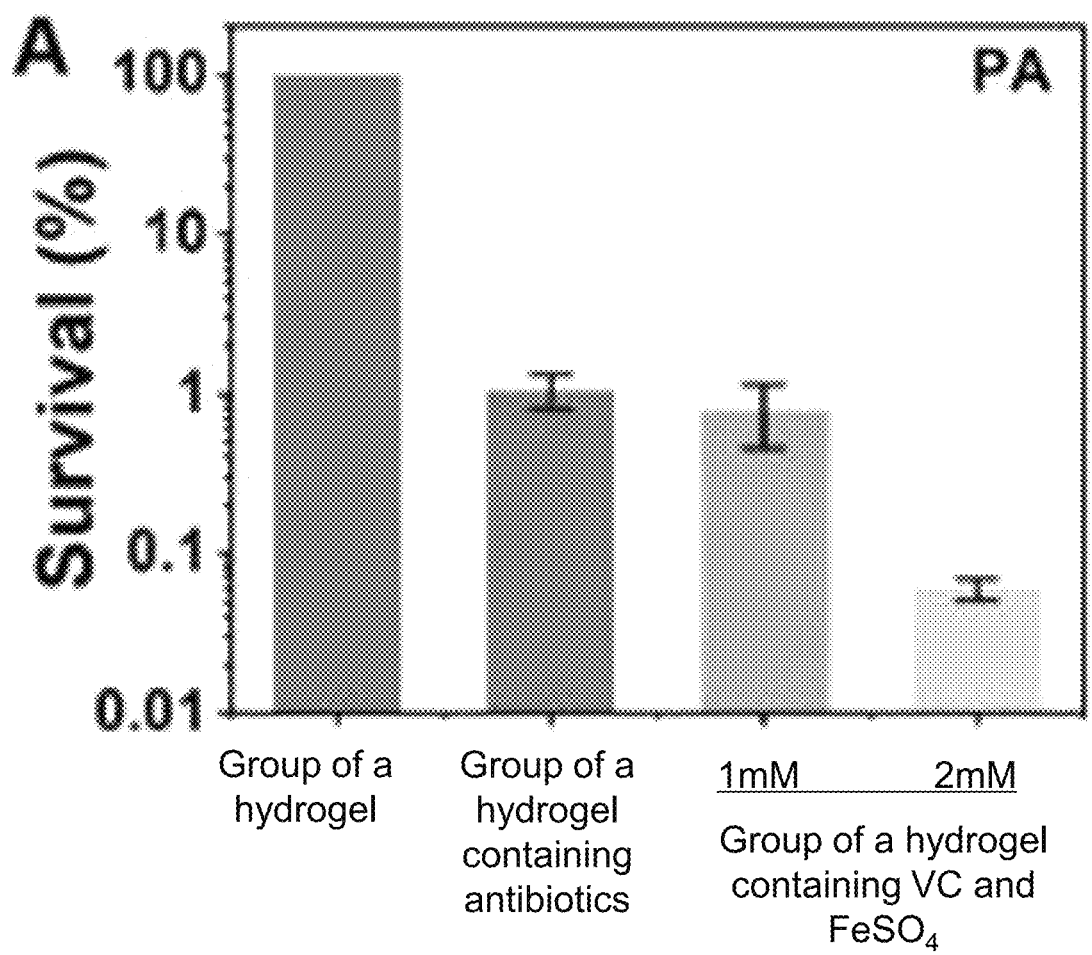
FIG. 2A and FIG. 2B are schematic diagrams illustrating in vitro bactericidal effects of the hydrogels of different treatment groups according to some embodiments of the present disclosure.
Figure 2B:
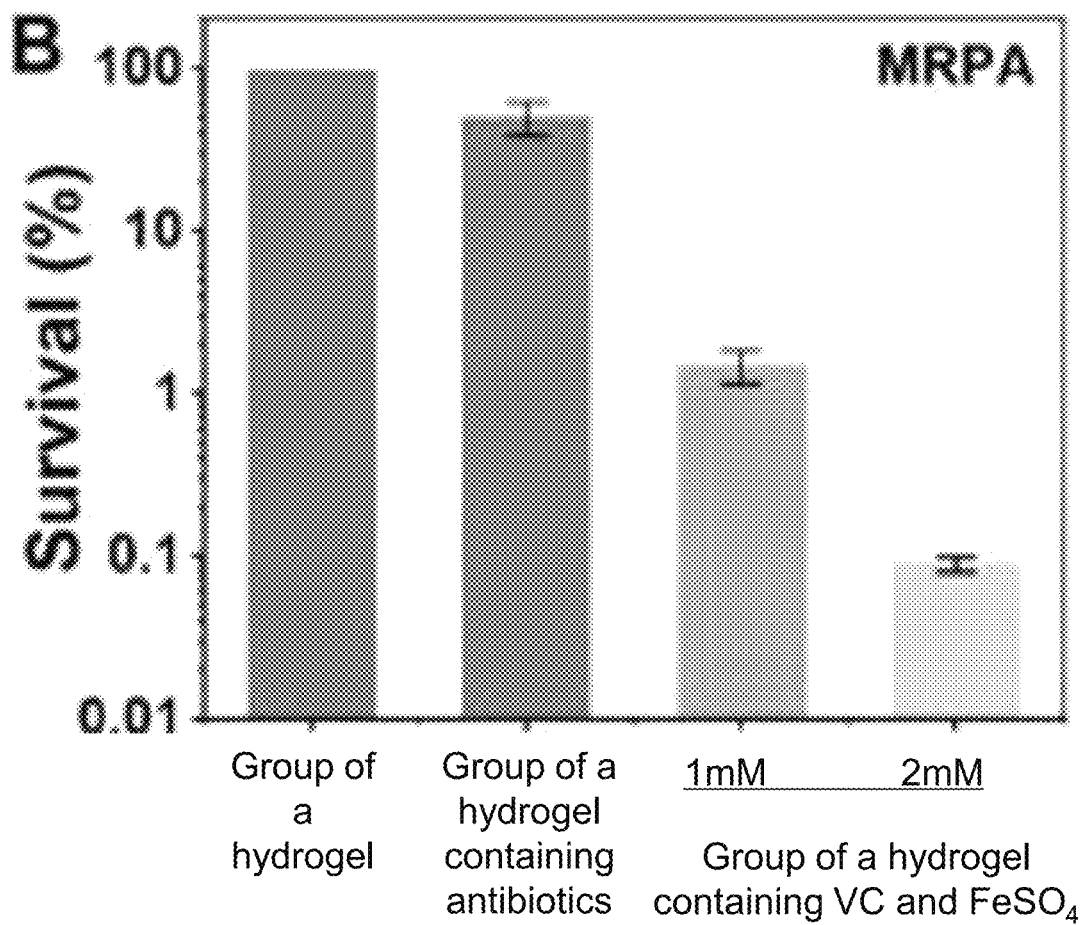

FIG. 2A and FIG. 2B are diagrams illustrating in vitro bactericidal effects of different treatment groups of hydrogels according to some embodiments of the present disclosure. FIG. 2A shows the bactericidal effect of hydrogels of different treatment groups on PA, and FIG. 2B shows the bactericidal effect of hydrogels of different treatment groups on MRPA. Results of FIG. 2A and FIG. 2B show that by simulating an in vitro surface contact experiment between PA and hydrogels containing ferrous ions, it is found that the hydrogel containing vitamin C and ferrous sulphate had good bactericidal effects on both PA and MRPA, especially the group of hydrogel containing 2 mM of vitamin C and ferrous sulphate, which has a bactericidal rate as high as 99.9% against both bacteria. For the group of the hydrogel containing antibiotics, while the ciprofloxacin hydrochloride is effective in eliminating common PA with a bactericidal rate of 99%, the hydrogel containing ciprofloxacin hydrochloride shows a bactericidal rate of only 50% when used for clinically-isolated drug-resistant bacteria, illustrating its ineffectiveness in responding to existing antibiotic crises, which is highly consistent with results of the available studies.

Example 2. Determination of Antimicrobial Model of a Ferrous Sulfate Hydrogel

To determine an antimicrobial mode of a hydrogel containing ferrous sulfate, the group of the hydrogel (100 μL), the group of the hydrogel containing antibiotics (100 μL), the group of the hydrogel containing 1 mM of vitamin C and ferrous sulfate (100 μL), and the group of the hydrogel containing 2 mM of vitamin C and ferrous sulfate (100 μL) were added into the centers of slides, respectively, and 5 μL of PA and MRPA ($10^8$ CFU/mL) washed with physiological saline were added vertically dropwise on a surface of hydrogels of each group, respectively. After incubation at 37° C. for 3 h, polyimide (PI; a final concentration of 1 μg/mL) was dropped on hydrogels containing PA cells or MRPA cells, and incubated at 37° C. for 20 min, and antimicrobial models of the hydrogels of each group were measured and determined using inverted fluorescence microscopy.

Figure 3:
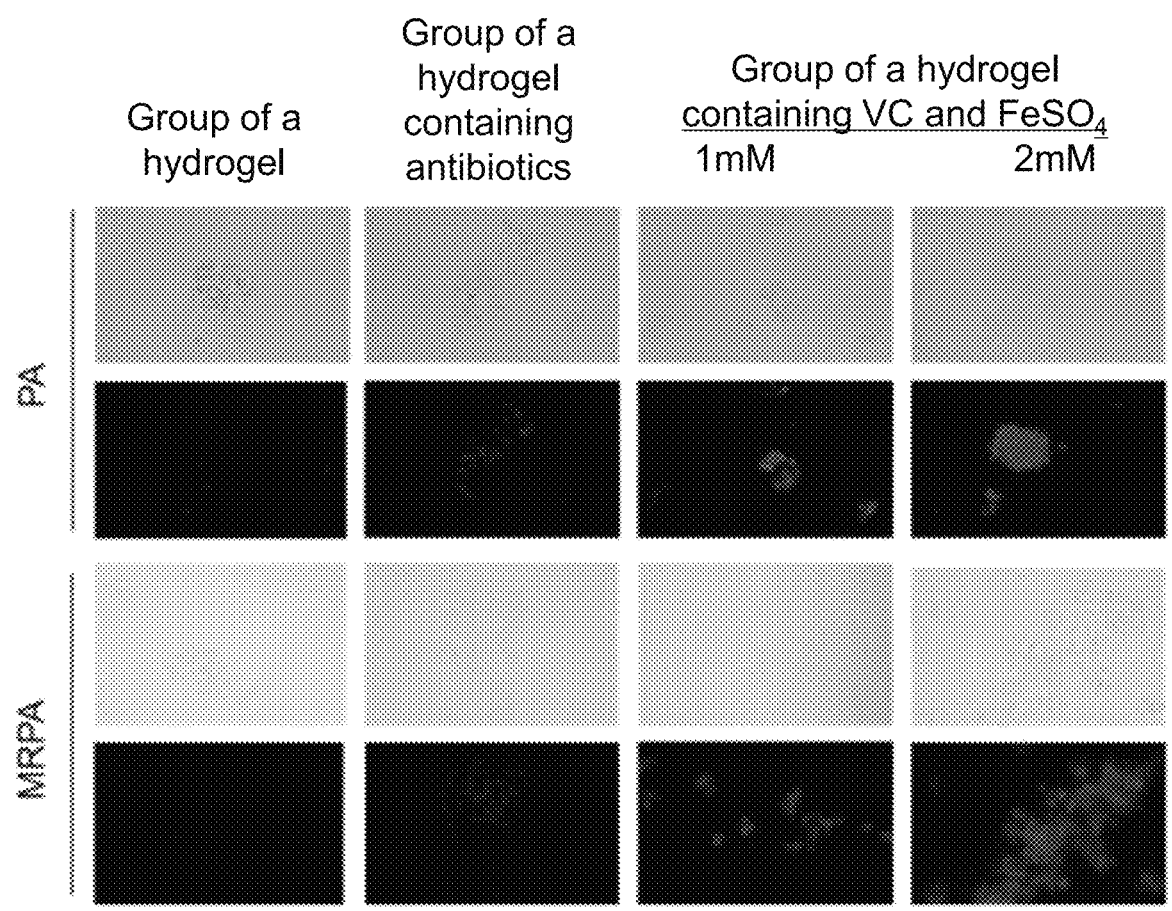
FIG. 3 is a fluorescent-stained micrograph illustrating bactericidal effects of the hydrogels of different treatment groups against *Pseudomonas aeruginosa* according to some embodiments of the present disclosure.

FIG. 3 is a fluorescent-stained micrograph illustrating bactericidal effects of hydrogels of different treatment groups against *Pseudomonas aeruginosa* according to some embodiments of the present disclosure. In FIG. 3, the first row from left to right shows white field diagrams of the bactericidal effect of different treatment groups of hydrogels on PA, respectively; the second row from left to right shows fluorescent-stained diagrams of the bactericidal effect of different treatment groups of hydrogels on PA, respectively; the third row from left to right shows white field diagrams of the bactericidal effect of different treatment groups of hydrogels on MRPA, respectively; the fourth row from left to right shows fluorescent-stained diagrams of the bactericidal effect of different treatment groups of hydrogels on MRPA, respectively. Results of FIG. 3 show that after being treated by the hydrogel containing vitamin C and ferrous sulfate, both PA and MRPA, after stained by PI, have significant red fluorescence production compared with the group of the hydrogel and the chromogenic reaction was more intense with the increase of concentration. Meanwhile, after treatment with antibiotics, common PA shows a strong fluorescence reaction, which confirms a bactericidal activity of antibiotics on common PA. However, for MRPA, antibiotic-treated bacteria also produced red fluorescence, but its fluorescence intensity is significantly weaker than that of the group of the hydrogel containing vitamin C and ferrous sulfate, indicating the group of the hydrogel containing antibiotic has a weaker bactericidal activity and may not effectively eliminate the multidrug-resistant bacteria, which reconfirms the ineffectiveness of antibiotics against the multidrug-resistant bacteria. Since these results are consistent with results in FIG. 2, it is proved again that the group of the hydrogel containing vitamin C and ferrous sulfate effectively eliminates PA and MRPA. In summary, the hydrogel containing ferrous compounds has the ability to replace antibiotics as a new antibacterial agent.

Example 3. Characterization and Conformational Detection of a Ferrous Sulfate Hydrogel The properties of the group of the hydrogel, the group of the hydrogel containing 1 mM of vitamin C and ferrous sulfate, and the group of the hydrogel containing 2 mM of vitamin C and ferrous sulfate were characterized through scanning electron microscopy (SEM) and Fourier Transform Infrared Spectrometer (FT-IR).

1 mL of the group of the hydrogel, 1 mL the group of the hydrogel containing 1 mM of vitamin C and ferrous sulfate, and 1 mL the group of the hydrogel containing 2 mM of vitamin C and ferrous sulfate were freeze-dried for at least 24 h, respectively, until the moisture of the hydrogels was completely evaporated, and ground the hydrogels into powder with liquid nitrogen for later use. A particle size and morphology of the hydrogels were observed using a field emission scanning electron microscopy (FESEM) with a voltage set at 20 Kv and a magnification at 500 times; a structure of the hydrogels was directly tested by an ATR mode of FT-IR, and the white powder obtained by freeze-drying of each group was milled and pressed with potassium bromide, a resolution of FT-IR was set to be 2 $cm^{-1}$ and a number of scans was set to be 32.

Figure 4:
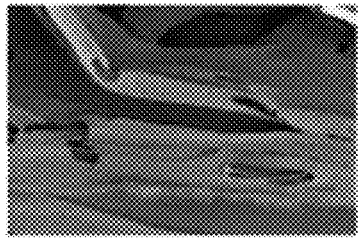
FIG. 4 is a diagram illustrating SEM images of the hydrogels of different treatment groups according to some embodiments of the present disclosure.
Figure 4:
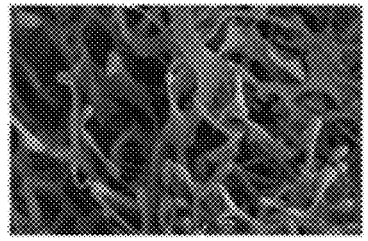
Figure 4:
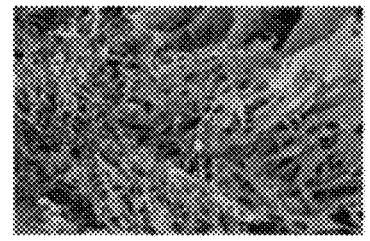

FIG. 4 is a diagram illustrating SEM images of hydrogels of different treatment groups according to some embodiments of the present disclosure. From left to right, SEM images of the group of the hydrogel, the group of the hydrogel containing 1 mM of vitamin C and ferrous sulfate, and the group of the hydrogel containing 2 mM of vitamin C and ferrous sulfate are shown, respectively. Results in FIG. 4 show that the addition of ferrous sulphate resulted in a more inhomogeneous porous structure of the hydrogel, and such porous structure facilitated the storage of a large amount of water in the hydrogel, which indicates that a sodium alginate-based ferrous sulphate hydrogel may have better water-holding and water-locking properties. Therefore, the hydrogel is suitable for the epidermis that has been dehydrated by a scald since it enables the epidermis to be sufficiently in the humid environment for skin generation.

Figure 5:
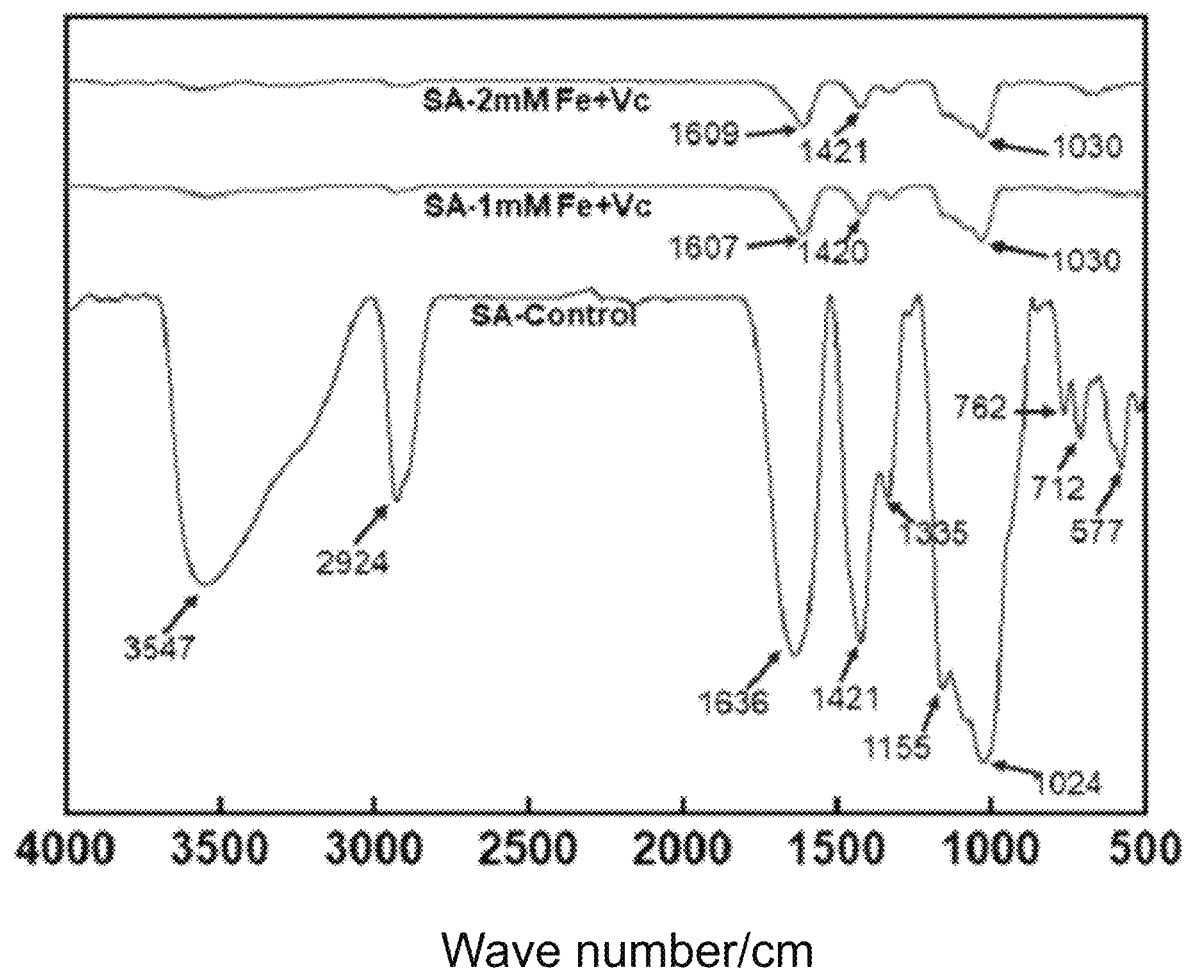
FIG. 5 is a diagram illustrating structural conformation of the hydrogels of different treatment groups detected by a Fourier Transform Infrared Spectrometer (FT-IR) according to some embodiments of the present disclosure.

Further, structural conformation of hydrogels at two concentrations was examined using FT-IR, as shown in FIG. 5. In FIG. 5, from bottom to top, there are the group of the hydrogel (SA-control), the group of the hydrogel containing 1 mM of vitamin C and ferrous sulfate (SA-1 mM Fe+Vc), and the group of the hydrogel containing 2 mM of vitamin C and ferrous sulfate (SA-2 mM Fe+Vc), respectively. Compared with the group of the hydrogel, an absorption peak of a group of a hydrogel containing vitamin C and ferrous sulfate shows a significant right shift at 1636 $cm^{-1}$ to 1607 $cm^{-1}$ (the group of the hydrogel containing 1 mM of vitamin C and ferrous sulfate) and to 1609 $cm^{-1}$ (the group of the hydrogel containing 2 mM of vitamin C and ferrous sulfate), which indicates that the C=C stretching bond is replaced by more H bonds to form a C—H bending vibration and indicates that the adding of ferrous sulfate endows the hydrogel with more moisture. In summary, the addition of ferrous sulfate can change the properties of the hydrogel, making the sodium alginate in the hydrogel has stronger water-locking and water-holding properties, which is favorable for the application in scald treatment.

Example 4. In Vivo Therapeutic Effect of a Ferrous Sulfate Hydrogel on Scald Infection Step 1, Constructing a Rat Scald Model With PA Infection
  (1) Thirty 6-8 week old male SD rats with a weight of 200 g-220 g were acclimatized and fed for 3-7 days;
  (2) Anesthesia: a mixture of ketamine-hydroxyzine of 0.3 mL/100 g was injected into peritoneal cavities of the SD rats. The dynamics of the SD rats were observed until their breathing was steady;
  (3) Scald model construction: the SD rats were initially depilated with a depilatory device, and depilatory ointment was used to fade the hair of the SD rats until their skins were bare and skin surfaces were smooth; a brass block with a diameter of 1 cm was placed in boiling water and the boiling water bath was carried out for 10 min until thermal equilibrium, and then the brass block was removed and placed on the epidermis of the SD rats, and left to stand for 2 min, then a deep second/third-degree scald model of the SD rats was constructed.
  (4) One hour after the deep second/third degree scald model of the SD rats was established, scalded necrotic tissue was removed using a biopsy perforator with a same diameter as a diameter of the scalded necrotic tissue to simulate removal of severely scalded skin clinically;
  (5) Infection: 50 µL of PA ($10^7$-$10^8$ CFU/mL) was added to wounds of the SD rats and the wounds were covered with a sterile medical patch to prevent foreign objects from entering the wounds and affecting observation. After the rats were fed for 1~2 days (25~30° C.), the wounds infected with PA were observed, and a PA-infected scald wound model was successfully constructed.

Step 2, Setting Processing Groups
  Scald group (Scald) (5 rats): rats were constructed with only the scald model, and a scald surface of the rats was cleaned daily with physiological saline, wiped with iodophor, and covered with a sterile medical patch.
  Infection group (PA infection) (5 rats): after the PA-infected scald wound model was successfully constructed on rats, a scald surface of the rats was cleaned daily with physiological saline, wiped with iodophor daily, and covered with sterile medical patch.
  Scald ointment group (Scald ointment) (5 rats): after the PA-infected scald wound model was successfully constructed on rats, a scald surface of the rats was cleaned daily with physiological saline, wiped with iodophor, and treated with a thick application of 1 mL of scald ointment, then subsequently covered with a sterile medical patch.
  Antibiotic group (Antibiotic) (5 rats): after the PA-infected scald wound model was successfully constructed on rats, a scald surface of the rats was cleaned daily with physiological saline, wiped with iodophor, and treated with 1 mL of hydrogel containing 1 mg/mL of ciprofloxacin hydrochloride, and subsequently covered with a sterile medical patch.
  Ferrous sulfate hydrogel group (SA-Fe+Vc) (5 rats): after the PA-infected scald wound model was successfully constructed on rats, a scald surface of the rats was cleaned daily with physiological saline, wiped with iodophor, and treated with a hydrogel containing vitamin C and ferrous sulfate (a hydrogel containing 1 mM of vitamin C and ferrous sulfate or a hydrogel containing 2 mM of vitamin C and ferrous sulfate), and then subsequently covered with a sterile medical patch.

Hydrogel group (SA) (5 rats): after the PA-infected scald wound model was successfully constructed on rats, a scald surface of the rats was cleaned daily with physiological saline, wiped with iodophor, and treated with 1 mL of the hydrogel, and then subsequently covered with a sterile medical patch.

Step 3, During pre-phase (0-10 days after infection): two treatments per day were performed at 12 h intervals; during post-phase (11-15 days): one treatment was performed per day and a photograph was taken to record wound healing.

Figure 6:
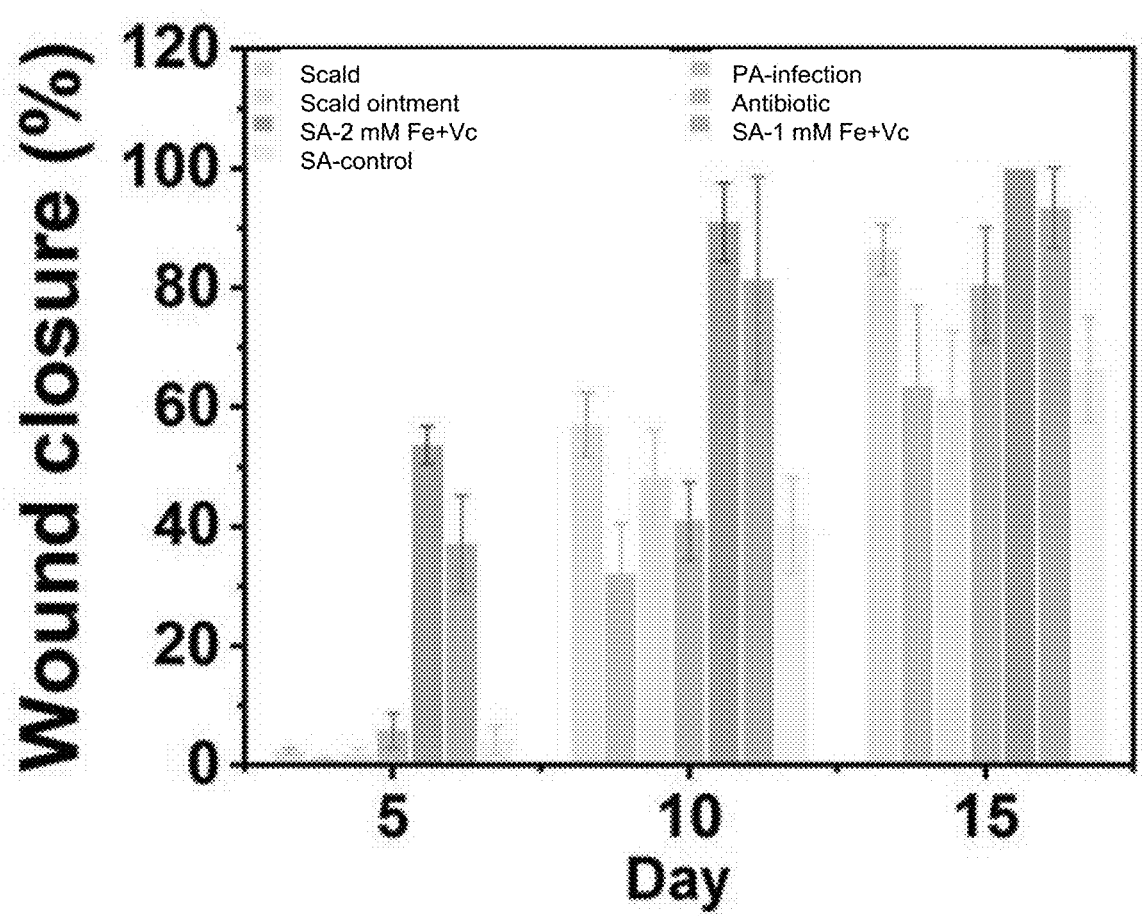
FIG. 6 is a diagram illustrating healing rate results of a PA-infected scald wound model on rats treated with different treatment manners according to some embodiments of the present disclosure.
Figure 7:
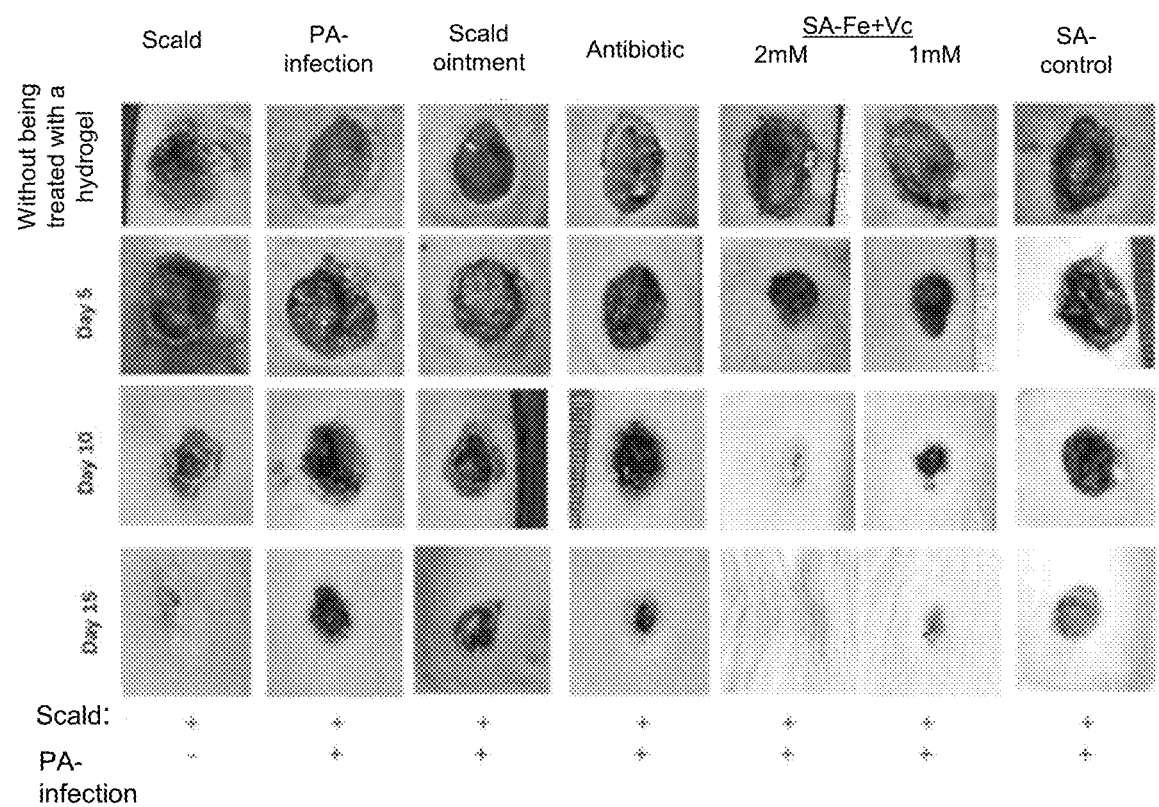
FIG. 7 is a diagram illustrating therapeutic effects of the PA-infected scald wound model on rats treated with different treatment manners after 5, 10, and 15 days according to some embodiments of the present disclosure.

Results of experiments on the healing of scalds with the hydrogel in rats are shown in FIG. 6 and FIG. 7. On the 5$^{th}$ day, the rats treated with the hydrogel containing vitamin C and ferrous sulfate have better wound healing ability than other groups, and wounds of the rats in the scald group still have more healing tissue accompanied by neoplastic granulation tissue production. Wounds of the rats in other PA-infected groups fail to be healed effectively, and the wounds are severely septic and hemorrhagic. Compared with the group of the hydrogel containing antibiotics, the group of a hydrogel containing vitamin C and ferrous sulfate are more favorable for wound healing in rats, with no pus or blood seen on the wounds, and the wound area is significantly smaller than the wound area on day 0 after infection. On the 10th day, the wounds of the rats treated with the hydrogel containing vitamin C and ferrous sulfate are basically completely healed, accompanied by a large amount of hair growth, and a healing rate is as high as 80% or more. The rats in remaining groups still have wound tissues with relatively large areas and trace amounts of pus and blood, which again suggests that the rats were severely infected with recurrent wound inflammation and slow recovery. On the 15th day, the wounds of rats treated with the hydrogel containing vitamin C and ferrous sulphate heal completely compared with the other groups, particularly, the scald wounds of rats treated with the hydrogel containing 2 mM of vitamin C and ferrous sulphate are completely healed, and a wound healing rate of the rats treated with the hydrogel containing 1 mM of vitamin C and ferrous sulphate reaches above 95% and the scalds is accompanied with a large number of hairs growth and complete generation of epidermis. However, the rats in the other groups have poor wound recovery, and the rats in the infection group still have more severe infections.

In summary, the hydrogel containing vitamin C and ferrous compound has an antimicrobial activity, which not only has a good bactericidal effect but also can effectively promote wound healing.

The basic concepts have been described above, and it is apparent to those skilled in the art that the foregoing detailed disclosure is intended as an example only and does not constitute a limitation of the present disclosure. Although not expressly stated herein, those skilled in the art may make various modifications, improvements, and amendments to the present disclosure. Such modifications, improvements, and amendments are suggested in the present disclosure, so such modifications, improvements, and amendments remain within the spirit and scope of the exemplary embodiments of the present disclosure.

At the same time, specific terms are employed to describe the embodiments of the present disclosure. Terms e.g., "an embodiment," "one embodiment," and/or "some embodiments" are intended to refer to one or more features, structures, or features associated with at least one embodiment of the present disclosure. Thus, it should be emphasized and noted that the terms "an embodiment," "one embodiment," or "an alternative embodiment," mentioned at different locations in the present disclosure two or more times, do not necessarily refer to a same embodiment. Additionally, certain features, structures, or features of one or more embodiments of the present disclosure may be appropriately combined.

Similarly, it should be noted that in order to simplify the presentation of the present disclosure, and thereby aid in the understanding of one or more embodiments of the invention, the preceding description of embodiments of the present disclosure sometimes incorporates a variety of features into a single embodiment, accompanying drawings, or description thereof. However, this method of disclosure does not imply that the objects of the present disclosure require more features than those mentioned in the claims. In fact, the embodiments have fewer features than all of the features of the single embodiment disclosed above.

In summary, it should be understood that the embodiments described in the present disclosure are intended only to illustrate the principles of the embodiments of the present disclosure. Other deformations may also fall within the scope of the present disclosure. Thus, by way of example and not limitation, alternative configurations of embodiments of the present disclosure may be considered consistent with the teachings of the present disclosure. Accordingly, the embodiments of the present disclosure are not limited to the embodiments expressly presented and described herein.

What is claimed is:

1. A method of preparing a ferrous sulfate hydrogel for treating scald infection caused by *Pseudomonas aeruginosa*, wherein the scald is a deep second-degree scald or a third-degree scald; the method comprising:
    S1, obtaining a mixed solution by dissolving ferrous sulfate and vitamin C at a molar concentration ratio of 1:1 in sterile ultrapure water, and heating the mixed solution to 50° C., wherein a molar concentration of the ferrous sulfate in the mixed solution is 2 mM; and
    S2, under a condition of heating, continuing to add sodium alginate powder whose mass constitutes 3.5% of a total mass of the mixed solution, stirring until the sodium alginate powder is dissolved and forming a stable colloid, and obtaining the ferrous sulfate hydrogel.

2. The method of claim 1, wherein the ferrous sulfate hydrogel is used as a therapeutic medication for the scald infection and/or a scald care product.

3. The method of claim 1, wherein the ferrous sulfate hydrogel further includes other medications for the treatment of the scald infection.

\* \* \* \* \*